US012491110B2

(12) United States Patent
Mandal et al.

(10) Patent No.: US 12,491,110 B2
(45) Date of Patent: Dec. 9, 2025

(54) HEATING PAD WITH STORAGE

(71) Applicant: Sunbeam Products, Inc., Atlanta, GA (US)

(72) Inventors: Lalit Mandal, Boca Raton, FL (US); Jill Walters, Delray Beach, FL (US)

(73) Assignee: Sunbeam Products, Inc., Atlanta, GA (US)

( * ) Notice: Subject to any disclaimer, the term of this patent is extended or adjusted under 35 U.S.C. 154(b) by 0 days.

(21) Appl. No.: 18/504,258

(22) Filed: Nov. 8, 2023

(65) Prior Publication Data

US 2024/0065885 A1 Feb. 29, 2024

Related U.S. Application Data

(63) Continuation of application No. 16/731,819, filed on Dec. 31, 2019, now abandoned.

(51) Int. Cl.
*A61F 7/08* (2006.01)
*A61F 7/00* (2006.01)

(52) U.S. Cl.
CPC ................ *A61F 7/08* (2013.01); *A61F 7/007* (2013.01); *A61F 2007/0088* (2013.01); *A61F 2007/0094* (2013.01); *A61F 7/0097* (2013.01)

(58) Field of Classification Search
CPC .......... A61F 7/007; A61F 7/0097; A61F 7/08; A61F 2007/0088; A61F 2007/0094
See application file for complete search history.

(56) References Cited

U.S. PATENT DOCUMENTS 6,488,149 B1 12/2002 Montagnino
6,969,831 B1 11/2005 Parker et al.
8,938,303 B1 1/2015 Matsen
2006/0052855 A1* 3/2006 Docherty ................ A61F 7/007 607/108
2006/0137072 A1* 6/2006 Visco ..................... A41D 23/00 2/127
2016/0059066 A1 3/2016 Willis
2017/0266485 A1 9/2017 Willis
2019/0038953 A1 2/2019 Bell et al.
2020/0359813 A1 11/2020 Lafleur et al.

* cited by examiner

*Primary Examiner* — Kaitlyn E Smith
*Assistant Examiner* — Bradford C. Blaise
(74) *Attorney, Agent, or Firm* — Husch Blackwell LLP

(57) ABSTRACT

The current invention provides a heating pad with a storage pouch and/or straps. The heating pad itself can store its controller and cord in a neat and compact manner within the pouch and/or secured by the straps or another fastener like a hook and loop fastener.

7 Claims, 5 Drawing Sheets

HEATING PAD WITH STORAGE

CROSS-REFERENCE TO RELATED APPLICATION

This Application is a continuation application that claims priority to the now-abandoned U.S. patent application Ser. No. 16/731,819, filed Dec. 31, 2019, entitled, "Heating Pad with Storage" which is incorporated herein by reference in its entirety.

FIELD OF THE INVENTION

The present invention relates generally to storage. More particularly, the invention relates to compact, neat storage for heating pads that may otherwise be haphazardly stored in a closet, cabinet or other location.

BACKGROUND OF THE INVENTION

Heating pads used to soothe pain or warm portions of a user's body on which the heating blanket is placed typically consist of three major components. There is the heating pad itself in varying sizes, a controller with push buttons to allow the user to control various aspects of the heating blanket, and a power cord of ranging length, often near nine feet long, that is plugged into wall while using the product.

Millions of consumers use heating pads on a regular basis. However, consumer surveys have shown that consumers find their use to be inconvenient and as a nuisance when storing the product after using it. The pad itself often comes in twelve inch by fifteen inch standard size, and a twelve inch by twenty-four inch larger size. The pads themselves are often not easily rollable or foldable and thus require space for storage. The controllers, which come in a size that fits into an adult hand, and the cord itself further add to the complexity of compactly storing the heating pad. Storing all these three parts needs space. Moreover, the controller and cord often become tangled and do not mesh well with the fabric layer of the heating pad when putting the pad away for storage prior to its next use.

Others have provided a separate zipped or cord-string bag in which a heating pad may be stored. Such a bag introduces yet another component, the bag itself. The bag can become lost, and it does not present a solution for neat, compact storage. Rather, it provides an opportunity for a user to haphazardly stuff the pad and its components into the bag.

SUMMARY OF THE INVENTION

This invention solves the aforementioned problems by integrating a storage pouch and/or straps into the heating pad. Then, the heating pad itself can store everything together in a neat and compact manner that improves product convenience and appearance.

In a first embodiment, a storage pouch is formed at one end of the heating pad in which the controller and the cord can be stored. Hook-and-loop fastening may be used to secure the pad in neat, compact storage form after rolling the pad with the components and cord stored in the pouch.

A second embodiment provides two elastic straps on one end of the heating pad cover. After the pad is rolled up with the controller and cord, the elastic straps may store the pad and its components in a neat, compact form.

In a third embodiment, the heating pad includes a storage pouch like that of the first embodiment, and it includes elastic straps like those of the second embodiment. After the pad with the controller and cord stored within the pocket is rolled up, the elastic strings may be wrapped around the rolled pad and components to keep the pad in a neat, compact form.

BRIEF DESCRIPTION OF THE DRAWINGS

For a better understanding of the present invention, reference may be made to the following accompanying drawings.

DETAILED DESCRIPTION OF THE INVENTION

Figure 1:
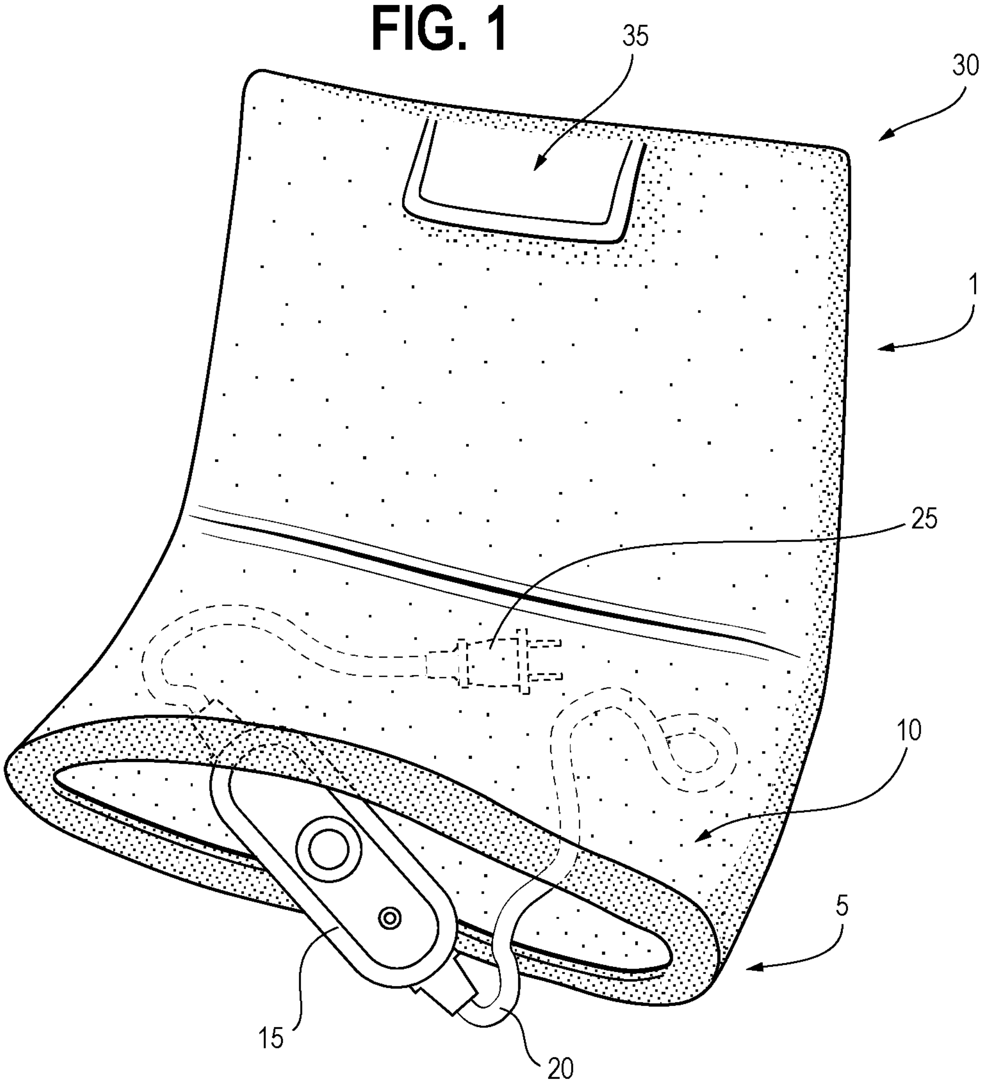
FIG. 1 is a perspective view of a first embodiment of a heating pad with storage constructed according to the teachings hereof.

Turning first to FIG. 1, a heating pad with storage 1, hereinafter referred to simply as heating pad 1, is illustrated. At one end portion 5 of the heating pad 1, a pouch 10 is formed within the heating pad 1. The pouch 10 may be used to store components of the heating pad 1 when the components are not in use. More particularly, a controller 15 for operating and adjusting heating components (not illustrated) of the heating pad 1 may be stored in the pouch 10 when not in use. Similarly, an electrical cord 20 and plug 25 that may be used to operate the controller 15 and/or the electrical components of the heating pad 1 may be stored within the pouch 10.

At a second end portion 30 opposite the first end portion 5 of the heating pad 1, an attachment means 35 may also be provided. In the illustrated embodiment, the attachment means 35 is a tab member member that uses a hook and loop fastener, as will be described herein below, to close the heating pad 1 in its stored, neat, compact form.

To get the heating pad 1 into its storage form (illustrated in FIG. 2), the controller 15, cord 20, and/or plug 25 may be stowed within the pouch 10. Thereafter, the first end portion 5 of the heating pad 1 may be rolled toward the second end portion 30 of the heating pad 1. Thereafter, the attachment means 35 in this case a tab member may be secured to the heating pad 1 in the manner illustrated in FIG. 2. In this configuration, the heating pad 1 is stored in a compact and neat fashion.

Figure 2:
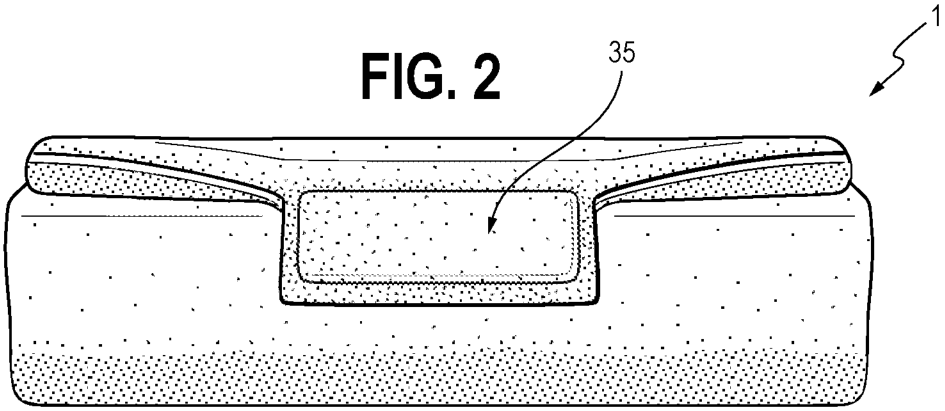
FIG. 2 is a front elevation view of the heating pad of FIG. 1 in its stored form.
Figure 3:
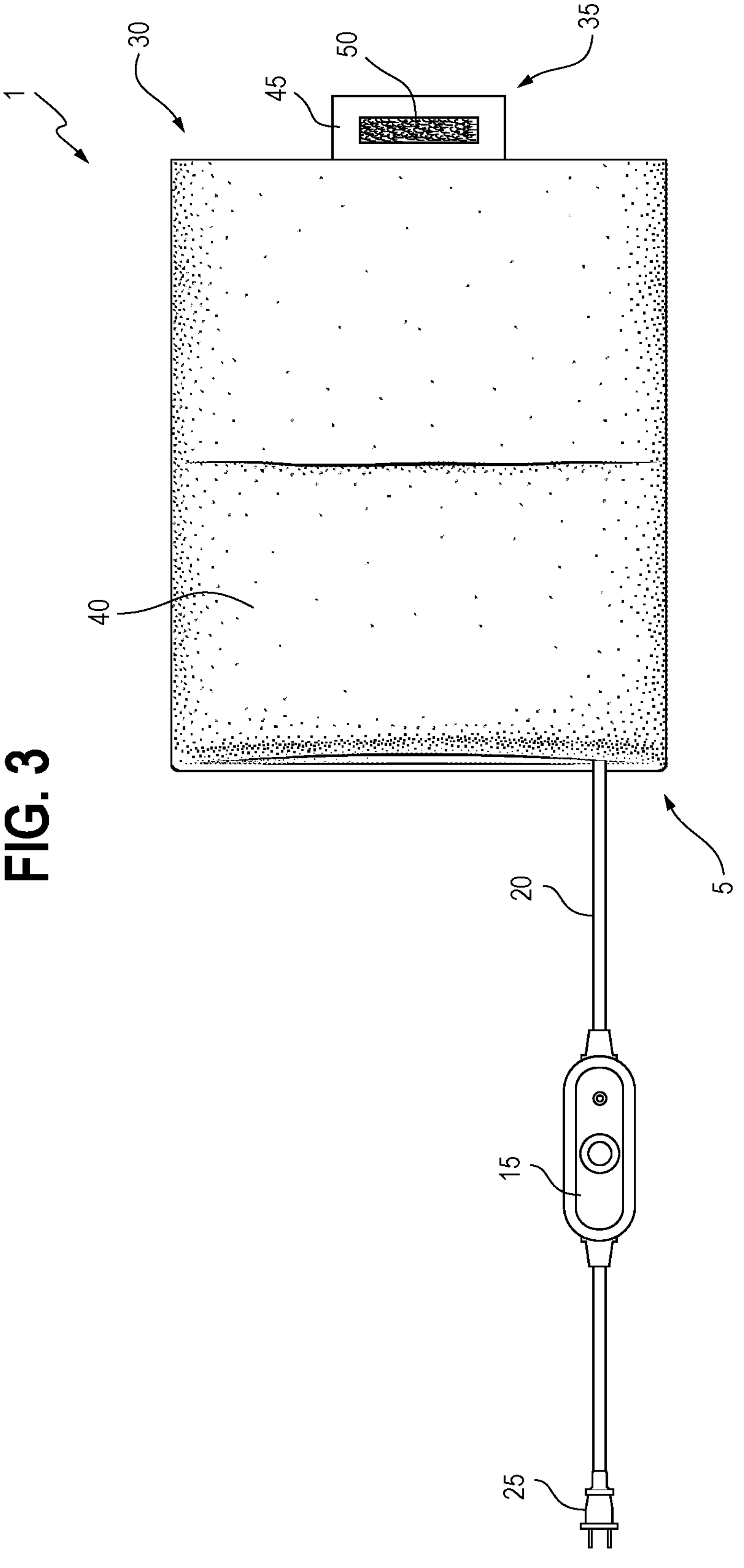
FIG. 3 is a top plan view of the heating pad of FIGS. 1 and 2.

Turning to FIG. 3, a top view of the heating pad 1 is provided. A top portion 40 of the heating pad 1 illustrated in FIG. 3 may be the side of the heating pad 1 that is away from the heating pad 1 when the heating pad 1 is in use, though in alternative embodiments, the top side 40 may also be in contact with a user when the heating pad 1 is in use. As illustrated in FIG. 3, a bottom side 45 of the attachment means 35 is preferably provided with a plurality of hook and loop fasteners 50. As will be described below, the hook and loop fasteners 50 may be used to secure the heating pad 1 in its rolled, compact, neat storage form illustrated in FIG. 2. In alternative embodiments, alternative fasteners may be used in place of the hook and loop fasteners 50, as one skilled in the art may appreciate.

Figure 4:
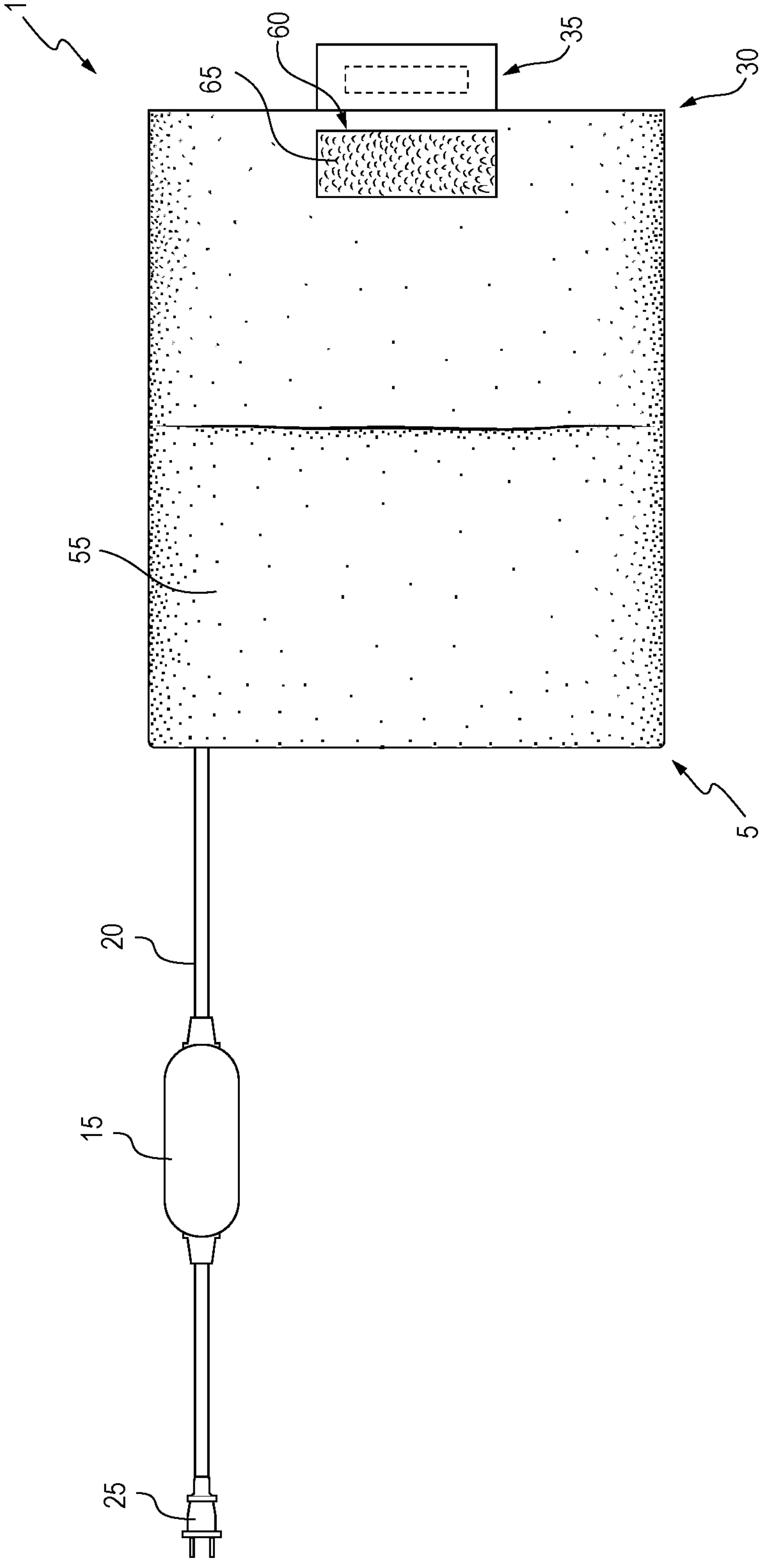
FIG. 4 is a bottom plan view of the heating pad of FIGS. 1-3.

In FIG. 4, the bottom of the heating pad 1, including a bottom side 55 of the heating pad 1, is illustrated in greater detail. The bottom side 55 of the heating pad 1 may be in contact with a user when the heating pad 1 is in use. However, as mentioned above, in some embodiments, the bottom side 55 and the top side 40 may be interchangeable such that the bottom side 55 faces away from a user when the heating pad 1 is in use. In the embodiment illustrated in FIG. 4, the bottom side 55 of the heating pad 1 is provided with an attachment member 60. The attachment member 60 is preferably provided adjacent the attachment means 35 near the second end portion 30 of the heating pad 1. In the illustrated embodiment, the attachment member 60 is comprised of a plurality of hook and loop fasteners 65. The hook and loop fasteners 65 are preferably substantially similar to the hook and loop fasteners 50 shown and illustrated in FIG. 3. As set forth above, like the hook and loop fasteners 50, the hook and loop fasteners 65 may be replaced with other suitable attachment means.

To securely store the controller 15, cord 20, and/or plug 25 within the heating pad 1, a user may place those same components within the pouch 10 before rolling the first end portion 5 toward the second end portion 30, as described above. When doing so, after sufficiently rolling the heating pad 1 such as shown in FIG. 2, the attachment means 35 and 60 preferably align with one another such that the hook and loop fasteners 50, 65 also align with one another. When the hook and loop fasteners 50, 65 align with one another, the attachment means 35, 60 may be attached to one another to secure the heating pad 1 in the storage position illustrated in FIG. 2.

Figure 5:
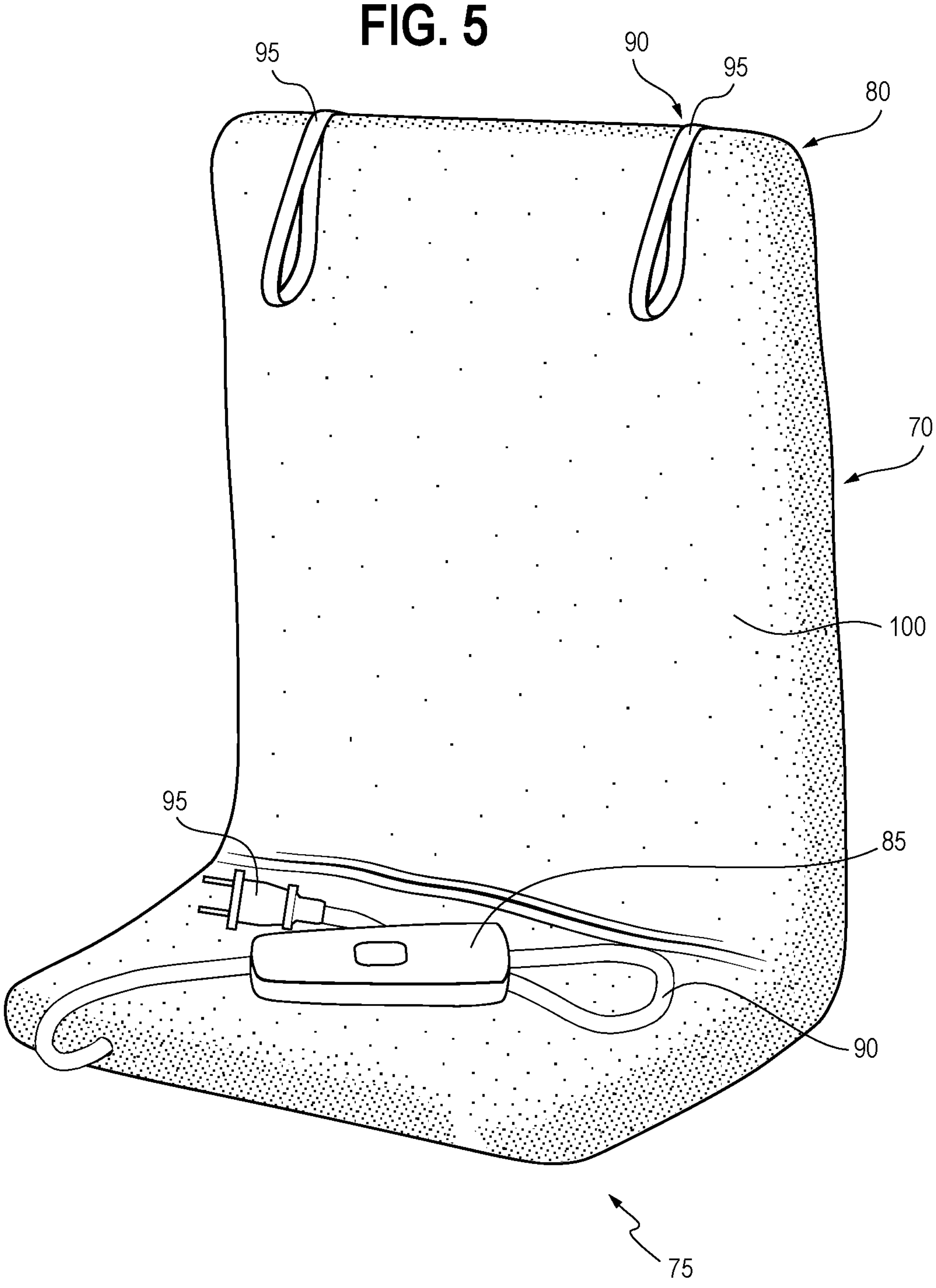
FIG. 5 is a perspective view of a second embodiment of a heating pad with storage constructed according to the teachings hereof.

Turning now to FIG. 5, an alternative heating pad with storage 70 is illustrated. The heating pad with storage 70 is referred to herein simply as heating pad 70. Like the heating pad 1, the heating pad 70 includes a first end portion 75 and a second end portion 80. The heating pad 70 also may include a controller 85, cord 90, and/or plug 95 that may be used to operate and control the heating pad 70. Unlike the heating pad 1, the alternative heating pad of FIG. 5 does not include a pouch. However, it does include an attachment means 90 that is embodied as two separately formed elastic loop members 95. In alternative embodiments, attachment means other than the elastic loop members 95 may be provided. In the illustrated embodiment, two elastic loop members 95 are provided, but in alternative embodiments, more or fewer elastic members such as the elastic loop members 95 may be provided. Further, in the illustrated embodiment, the elastic loop members 95 are sewn to the second end portion 80 of the heating pad 70. In alternative embodiments, the elastic loop members 95 may be permanently or semi-permanently attached to the end portion 80 using alternative, foreseeable means.

Figure 6:
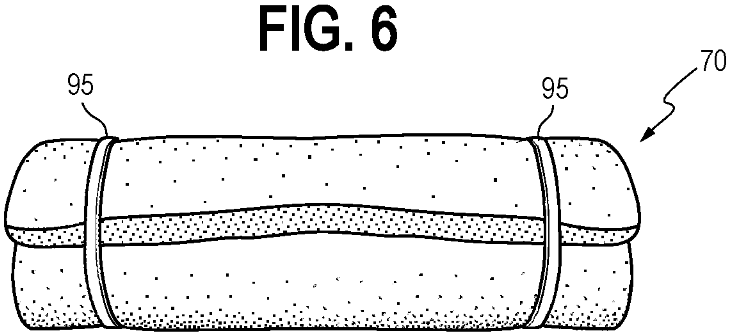
FIG. 6 is a front elevation view of the heating pad of FIG. 5 in its stored form.

To store the heating pad 70 in the compact, neat manner illustrated in FIG. 6, the controller 85, cord 90 and/or plug 95 should first be placed within the heating pad 70. It should be noted that in FIG. 5, the controller 85, cord 90, and plug 95 are placed on a first side 100 of the heating pad 70, but in alternative embodiments, may just as easily be placed on a second side (not illustrated) opposite the first side 100. Subsequently, the first end portion 75 of the heating pad 70 may be rolled toward the second end portion 80. When the first end portion 75 has been sufficiently rolled to the second end portion 80, the elastic loop members 95 may be wrapped around the entirety of the heating pad 70, as shown in FIG. 6. When the elastic loop members 95 are used to store the heating pad 70 in the neat, compact form of FIG. 6, they also may be easily removed from the heating pad 70 to unroll the heating pad 70 when a user wishes to use the heating pad 70.

Figure 7:
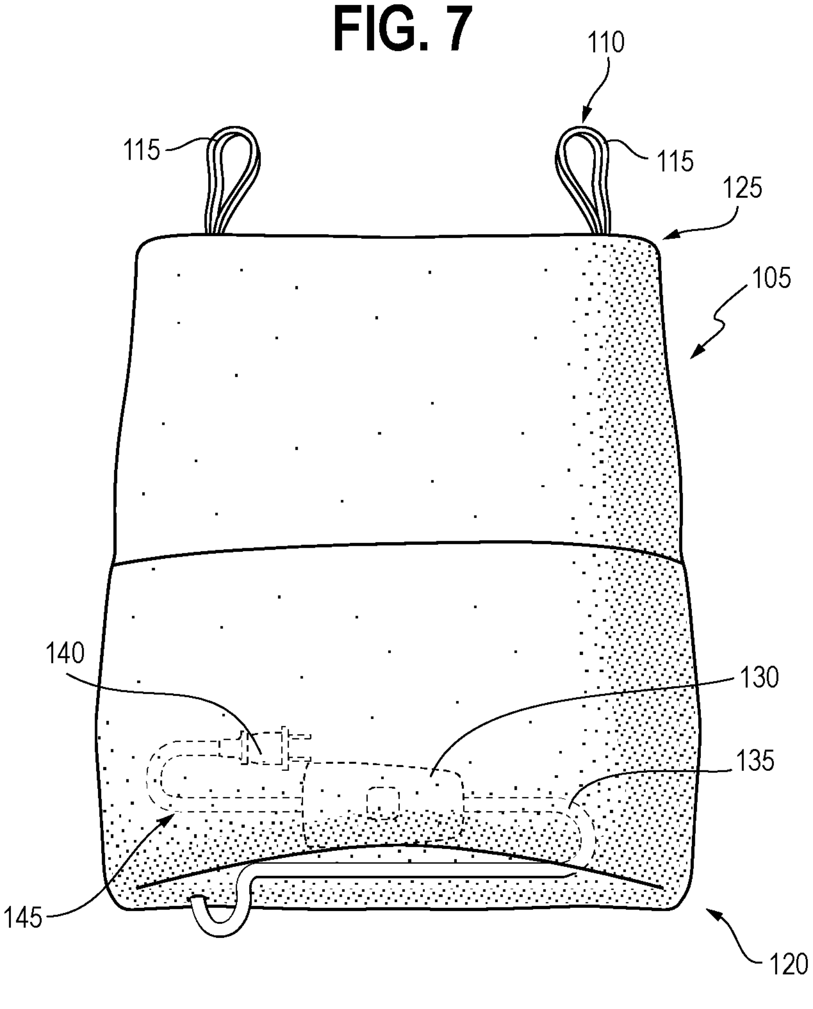
FIG. 7 is a perspective view of a third embodiment of a heating pad with storage constructed according to the teachings hereof.

In FIG. 7, one additional embodiment of a heating pad with storage 105, hereinafter heating pad 105, is provided. The heating pad 105 is substantially similar to the heating pad 70 in that it includes attachment means 110 embodied as elastic members 115. It further includes a first end portion 120 and a second end portion 125. It also may include a controller 130, cord 135, and/or plug 140 to operate the heating pad 105. Unlike the heating pad 70, however, and like the heating pad 1, the heating pad 105 is preferably provided with a pouch 145 that may be used to secure the controller 130, cord 135, and/or plug 140 therein.

In operation, to store the heating pad 105, the controller 130, cord 135, and/or plug 140 may be stored in the pouch 145 before rolling the first end portion 120 of the heating pad 105 toward the second end portion 125. Thereafter, the attachment means 110, embodied as elastic loop members 115 may be used to store and secure the heating pad 105 in substantially the same manner as described and illustrated for FIG. 6.

From the foregoing, it will be seen that the various embodiments of the present invention are well adapted to attain all the objectives and advantages hereinabove set forth together with still other advantages which are obvious and which are inherent to the present structures. It will be understood that certain features and sub-combinations of the present embodiments are of utility and may be employed without reference to other features and sub-combinations. Since many possible embodiments of the present invention may be made without departing from the spirit and scope of the present invention, it is also to be understood that all disclosures herein set forth or illustrated in the accompanying drawings are to be interpreted as illustrative only and not limiting. The various constructions described above and illustrated in the drawings are presented by way of example only and are not intended to limit the concepts, principles, and scope of the present invention.

Many changes, modifications, variations, and other uses and applications of the present invention will, however, become apparent to those skilled in the art after considering the specification and the accompanying drawings. All such changes, modifications, variations, and other uses and applications which do not depart from the spirit and scope of the invention are deemed to be covered by the invention, which is limited only by the claims which follow.

The invention claimed is:

1. A heating pad with storage, the heating pad comprising:
- at least four sides defining a perimeter of the heating pad;
- a cord and a controller for operating a heating function of the heating pad;
- an attachment mechanism located at one end portion of the heating pad to retain the heating pad in a rolled up form when the heating pad is rolled;
- an exterior formed by an upper surface and a lower surface, wherein the upper surface and the lower surface are each formed by the at least four sides, and wherein the upper surface includes a first innermost surface, and the lower surface includes a second innermost surface; and
- a pouch formed within one of the at least four sides and formed by the first innermost surface and the second innermost surface, wherein the pouch is configured to receive the cord and the controller such that the cord and the controller are configured to be secured for storage in the pouch;

wherein the cord and the controller are in one of a stored position or an un-stored position;

wherein, in the stored position, both the cord and the controller are positioned within the pouch; and wherein, in the un-stored position, the cord is at least partially positioned within the pouch.

2. The heating pad of claim 1, wherein the attachment mechanism is a hook and loop fastener.

3. The heating pad of claim 1, wherein the attachment mechanism is one or more elastic loops.

4. A heating pad with storage, the heating pad comprising:

at least four sides defining a perimeter of the heating pad;

a cord and a controller for operating a heating function of the heating pad;

an exterior formed by an upper surface and a lower surface, wherein the upper surface and the lower surface are each formed by the at least four sides, and wherein the upper surface includes a first innermost surface, and the lower surface includes a second innermost surface; and a pouch formed within one of the at least four sides and formed by the first innermost surface and the second innermost surface, wherein the pouch is configured to receive the cord and the controller such that the cord and the controller are configured to be secured for storage in the pouch;

wherein the cord and the controller are in one of a stored position or an un-stored position;

wherein, in the stored position, both the cord and the controller are positioned within the pouch; and wherein, in the un-stored position, the cord is at least partially positioned within the pouch.

5. The heating pad of claim 4, further comprising a hook and loop fastener located at one end portion of the heating pad to retain the heating pad in a rolled up form when the heating pad is rolled.

6. The heating pad of claim 4, further comprising one or more elastic loops located at one end portion of the heating pad to retain the heating pad in a rolled up form when the heating pad is rolled.

7. The heating pad of claim 4, wherein the pouch is located on an end portion of one of the first side and the second side of the heating pad.

* * * * *